US011783102B2

(12) United States Patent
Dayal et al.

(10) Patent No.: US 11,783,102 B2
(45) Date of Patent: Oct. 10, 2023

(54) PREDICTIVE MODELING PLATFORM FOR SERIAL CASTING TO CORRECT ORTHOPEDIC DEFORMITIES

(71) Applicant: Children's National Medical Center, Washington, DC (US)

(72) Inventors: Anuradha Dayal, Washington, DC (US); Reza Monfaredi, Rockville, MD (US); Kevin Cleary, Potomac, MD (US); Matthew Oetgen, Chevy Chase, MD (US)

(73) Assignee: BabySteps Orthopedics Inc., Wilmington, DE (US)

( * ) Notice: Subject to any disclaimer, the term of this patent is extended or adjusted under 35 U.S.C. 154(b) by 210 days.

(21) Appl. No.: 16/864,099

(22) Filed: Apr. 30, 2020

(65) Prior Publication Data

US 2020/0349308 A1 Nov. 5, 2020

Related U.S. Application Data

(60) Provisional application No. 62/841,012, filed on Apr. 30, 2019.

(51) Int. Cl.
*G06F 30/27* (2020.01)
*G06T 19/20* (2011.01)
(Continued)

(52) U.S. Cl.
CPC ............ *G06F 30/27* (2020.01); *A61F 5/0127* (2013.01); *G06F 30/23* (2020.01); *G06T 19/20* (2013.01);
(Continued)

(58) Field of Classification Search
CPC ...... G06F 30/00; G06F 30/27; G06F 2111/16; G16H 50/50; G16H 30/40; G16H 20/30;
(Continued)

(56) References Cited

U.S. PATENT DOCUMENTS 6,701,174 B1 * 3/2004 Krause .................... G06T 17/10
600/407
7,386,428 B1 * 6/2008 Hallquist ................ G06F 30/23
703/2

(Continued)

FOREIGN PATENT DOCUMENTS

WO 2019/157486 A1 8/2019

OTHER PUBLICATIONS

Ganesan et al., A novel 3D evaluation method for assessing bone to bone relationships in clubfoot. Eur Rev Med Pharmacol Sci. Mar. 2019;23(5):1882-1890.
(Continued)

*Primary Examiner* — Charles L Beard
(74) *Attorney, Agent, or Firm* — McCarter & English, LLP

(57) ABSTRACT

A system and method are provided herein for modeling of force vectors for serial casts to correct orthopedic deformities includes a camera configured to capture a three-dimensional image of the deformity, a computing device programmed to generate a three-dimensional model of the deformity based on the image of the deformity, determine the boundary conditions for the deformity based on the three-dimensional image of the deformity, and generate force vectors for a series of casts to correct the deformity. In exemplary embodiments, the system can print a series of casts to correct the deformity.

13 Claims, 15 Drawing Sheets

(51) Int. Cl.
*G06F 30/23* (2020.01)
*A61F 5/01* (2006.01)
*G16H 30/40* (2018.01)
*G06F 111/16* (2020.01)

(52) U.S. Cl.
CPC .......... *G16H 30/40* (2018.01); *G06F 2111/16* (2020.01); *G06T 2210/41* (2013.01)

(58) Field of Classification Search
CPC .. A61F 2002/5049; A61F 5/01; A61F 5/0127; A61F 5/0111; A61F 5/14; A43D 2200/60; A43D 1/02; G06T 19/20; G06T 2207/10088; G06T 17/00; G06T 2200/04; G06T 2207/30052; G06T 2219/2021; G06T 2219/20; G06T 2207/10081; G06T 2207/10096; G06T 2210/41; G06T 30/00; G06N 3/08

See application file for complete search history.

(56) References Cited

U.S. PATENT DOCUMENTS

| | | | |
|---|---|---|---|
| 7,569,023 | B2 | 8/2009 | Dobbs |
| 3,083,703 | A1 | 12/2011 | Daizade |
| 8,814,815 | B2 | 8/2014 | DeHeer et al. |
| 11,389,248 | B1* | 7/2022 | Roh .................. A61B 34/20 |
| 2006/0070260 | A1* | 4/2006 | Cavanagh ............ G16H 50/50 36/44 |
| 2009/0306801 | A1* | 12/2009 | Sivak ................... A61F 5/0113 700/118 |
| 2011/0087465 | A1* | 4/2011 | Mahfouz .............. G06F 16/285 703/2 |
| 2013/0226059 | A1* | 8/2013 | Morris ................. A61F 5/0111 602/27 |
| 2014/0180185 | A1* | 6/2014 | Zachariasen ........... B33Y 50/02 602/5 |
| 2016/0022466 | A1* | 1/2016 | Pedtke ................. A61F 5/0127 700/98 |
| 2016/0101571 | A1* | 4/2016 | Schouwenburg ...... B33Y 50/00 602/5 |
| 2016/0101572 | A1* | 4/2016 | Schouwenburg ...... B33Y 80/00 602/5 |
| 2016/0331071 | A1* | 11/2016 | Kane .................... A43B 17/00 |
| 2017/0091411 | A1* | 3/2017 | Schoenecker ......... G16H 20/30 |
| 2017/0116360 | A1* | 4/2017 | Han ....................... G06F 30/23 |
| 2017/0228859 | A1* | 8/2017 | Schouwenburg ...... A43B 17/02 |
| 2017/0280828 | A1* | 10/2017 | Berger ..................... A43D 3/00 |
| 2017/0360578 | A1* | 12/2017 | Shin ..................... G09B 23/286 |
| 2018/0157228 | A1* | 6/2018 | Spector ............... A43B 17/006 |
| 2018/0177624 | A1* | 6/2018 | Vlasic .................... A43B 7/141 |
| 2018/0289423 | A1* | 10/2018 | Singh ..................... A61B 34/10 |
| 2019/0231578 | A1* | 8/2019 | Ranganathan ............ A61F 5/14 |
| 2019/0261733 | A1* | 8/2019 | Schouwenburg ...... A43B 7/143 |
| 2019/0283394 | A1* | 9/2019 | Ashcroft .................. A43B 5/06 |
| 2020/0151594 | A1* | 5/2020 | Schwartz ............... G06N 20/00 |
| 2020/0214870 | A1* | 7/2020 | Washizu .................... A61F 5/01 |
| 2020/0238626 | A1* | 7/2020 | Bleicher .................... A61F 5/14 |
| 2020/0245724 | A1* | 8/2020 | Kobe ..................... A61B 6/032 |
| 2020/0349308 | A1* | 11/2020 | Dayal .................... G06F 30/23 |
| 2020/0357508 | A1* | 11/2020 | Deleu .................... G16H 50/50 |
| 2020/0390503 | A1* | 12/2020 | Casas .................... A61B 34/20 |
| 2021/0042458 | A1 | 2/2021 | Dayal et al. |
| 2021/0145608 | A1* | 5/2021 | Herr ..................... A61B 8/0825 |
| 2021/0177089 | A1* | 6/2021 | Schouwenburg ...... A43B 7/143 |
| 2021/0315323 | A1* | 10/2021 | Hakkala ................. A61B 5/107 |
| 2022/0068016 | A1* | 3/2022 | Raz ........................ G06T 17/00 |
| 2022/0237880 | A1* | 7/2022 | Juppe ..................... G06T 17/00 |
| 2022/0331344 | A1* | 10/2022 | Greenbaum ......... A61K 31/675 |

OTHER PUBLICATIONS

Gozar et al., Finite-element-based 3D computer modeling for personalized treatment planning in clubfoot deformity: Case report with technique description. Medicine (Baltimore). Jun. 2018;97(24):e11021, 7 pages.

Gozar et al., Medical Use of Finite Element Modeling of the Ankle and Foot. Journal of Interdisciplinary Medicine. Jan. 29, 2018, 5 pages, pre-publicaiton edition. DOI: 10.1515/jim-2018-0001.

Jain et al., Biomodeling of clubfoot deformity of babies. Rapid Prototyping Journal. May 29, 2009;15(3):164-170.

Khas et al., Development of an orthosis for simultaneous three-dimensional correction of clubfoot deformity. Clin Biomech (Bristol, Avon). Jan. 2018;51:67-75.

Manak et al., 3D Modeling of Shape Geometry of Talus of Clubfoot (CTEV). Foot Ankle Stud. 2018;2(1):1012, 5 pages.

International Search Report and Written Opinion for Application No. PCT/US2020/058597, dated Feb. 11, 2021, 13 pages.

International Preliminary Report on Patentability for Application No. PCT/US2020/058597, dated May 12, 2022, 10 pages.

Desai et al., Bracing in the treatment of children with clubfoot: past, present, and future. Iowa Orthop J. 2010:30:15-23.

Ganesan et al., Developing a Three-Dimensional (3D) Assessment Method for Clubfoot—A Study Protocol. Front Physiol. Jan. 4, 2018;8:1098, 11 pages.

Giesberts et al., Ten cold clubfeet. Acta Orthop. Oct. 2018;89(5):565-569.

GRABCAD Community, 3D printed cast for the Ponseti Method. Retrieved online at: https://grabcad.com/library/3d-printed cast-for-the-ponseti-method-1. 4 pages, Jan. 28, 2019.

Howren et al., Early ultrasonographic evaluation of idiopathic clubfeet treated with manipulations, casts, and Botox (®): a double-blind randomized control trial. J Child Orthop. Feb. 2015;9(1):85-91.

Krivonlak et al., 3D Printed Custom Orthotic Device Development: A Student-driven Project. 2017 ASEE Annual Conference & Exposition. 12 pages, Jun. 2017.

Nichols, The Ponseti Method: Bracing Phase. KidsHealth, retrieved online at: https://kidshealth.org/en/parents/ponseti-bracing.html. 4 pages, Feb. 2022.

Savonen et al., Open-Source Three-Dimensional Printable Infant Clubfoot Brace. Journal of Prosthetics and Orthotics. 21 pages, (2019). pre-print. doi: 10.1097/JPO.0000000000000257.

Steps Clubfoot Care, The clubfoot brace. Retrieved online at: https://steps.org.za/bracewear/. 3 pages, (2016).

Wallander, Congenital clubfoot. Aspects on epidemiology, residual deformity and patient reported outcome. Acta Orthop Suppl. Feb. 2010;81(339):1-25.

* cited by examiner

PREDICTIVE MODELING PLATFORM FOR SERIAL CASTING TO CORRECT ORTHOPEDIC DEFORMITIES

CROSS REFERENCE TO RELATED APPLICATIONS

The present application claims the benefit of U.S. Provisional Patent Application No. 62/841,012, filed on Apr. 30, 2019, which is incorporated herein by reference in its entirety.

BACKGROUND

Conventionally, common pediatric orthopedic deformities such as Talipes equinovarus or congenital talipes equinovarus (commonly called clubfoot) have been difficult to treat because of difficulties with access to care and relative subjectivity of treatment. In the case of clubfoot, the current standard of care afforded to correct this skeletal deformity is the Ponseti serial casting methodology, in which the deformity is corrected using a weekly series of casts. Limitations of this method include the need for highly trained surgeons proficient in this method and frequent weekly visits to the orthopedic surgeon for placement of the casts. Even when skilled doctors trained in the method are available, there is a lot of variability and subjectivity in determining the next step of the serial cast. Variability in casting technique and inability to predict treatment length lead to difficulties in standardization of the treatment course of serial clubfoot correction.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1A:
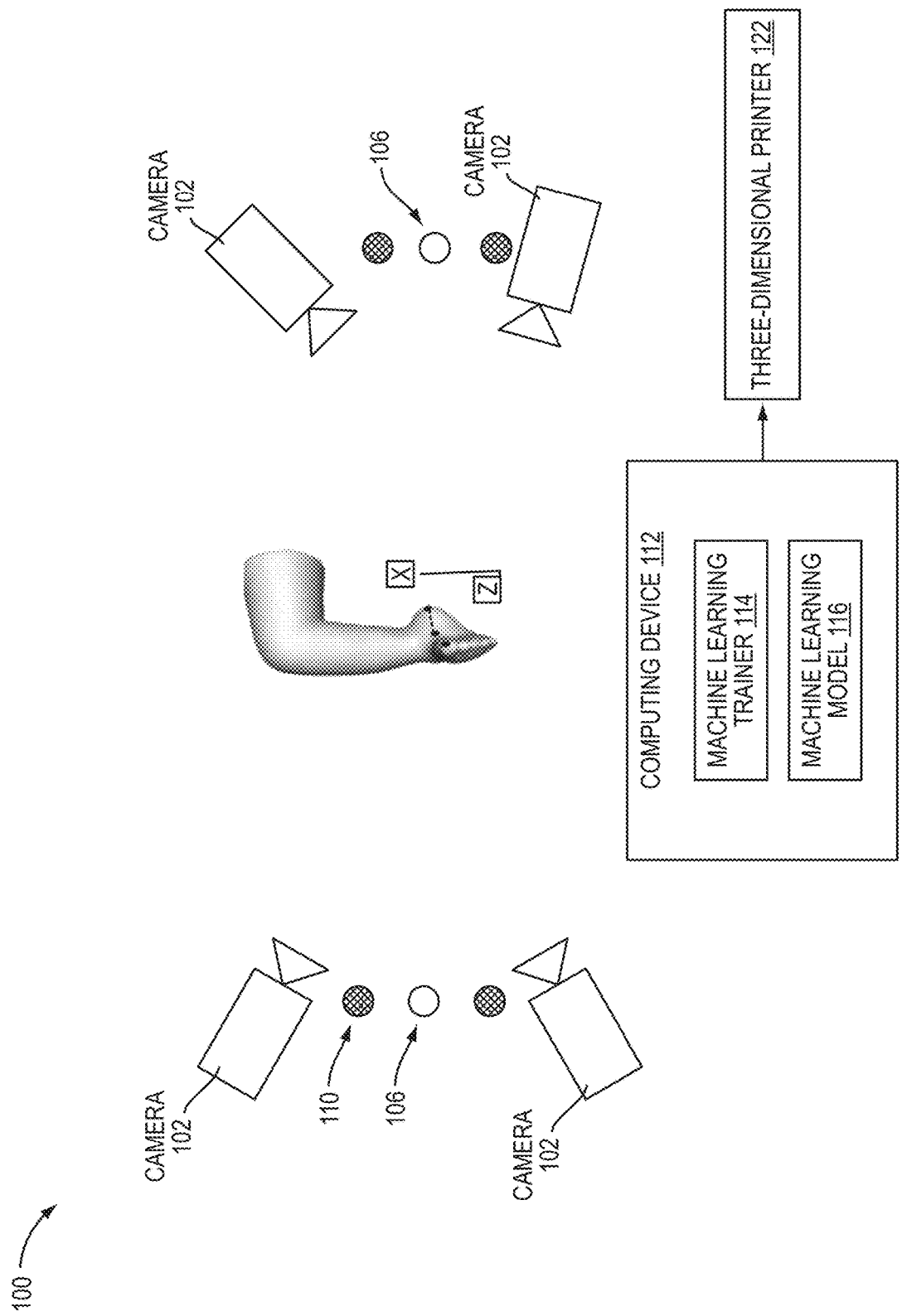
FIG. 1A is a block diagram illustrating a system for modelling force vectors for serial casts to correct orthopedic deformities in accordance with various embodiments taught herein.

Serial casting corrects a three-dimensional deformity of clubfoot through weekly manipulation of the deformity of the foot in a step-wise process. Often times correction is in multiple three-directional planes simultaneously. Conventionally, this manipulation is a very manual process, labor intensive and embodies an imprecise prediction of subsequent steps and outcomes. Although, computer modelling for serial casts to correct orthopedic deformities exists, the conventional computer modeling requires a linear approach of approximating a series of points and lines to determine a specific direction in which a cast in the series of casts applies a force to the deformity. However, the linear approach does not account for the three-dimensional deformities of the clubfoot within the cavus, adductus, varus, equinus and derotational elements.

Embodiments of the present disclosure include systems and methods for modelling of force vectors for a cast or a series of casts to correct orthopedic deformities that overcome the difficulties and problems described herein with respect to conventional techniques. In exemplary embodiments, the system includes a camera configured to capture a three-dimensional image of the deformity, a computing device programmed to generate a three-dimensional model of the deformity based on the image of the deformity, determine boundary conditions for the deformity based on the three-dimensional image of the deformity, and generate force vectors for a series of casts to correct the deformity. In exemplary embodiments, the system can provide instructions or data to print a three-dimensional cast or a series of casts to correct the deformity.

In exemplary embodiments, boundary conditions can be the desired angles of the corrected deformity for the next cast or the final desired correction or both. In exemplary embodiments, the system can determine the force vectors for the series of casts to correct the deformity based on the boundary conditions, and finite element analysis of the forces. A series of simulations based on trial force vectors can be processed to arrive at the desired force vector or set of vectors for a cast or a series of casts.

In exemplary embodiments, the camera can be an array of cameras, an ultrasound system, a three-dimensional scanner, a magnetic resonance imaging device, a CT scanner and the like. For example, the system can use an array of cameras configured to capture a series of images and stich the series of images to generate a three-dimensional model of the deformity.

In exemplary embodiments, the system can be configured to determine the boundary conditions of the deformity based on a machine learning model. The boundary conditions of the deformity can be the desired angle of correction for the deformity. For example, the machine learning model can be trained based on prior patient data for a plurality of patients such as an original three-dimensional image of the deformity, images of intermediate stages of correction of the deformity and the final image of the corrected deformity. In exemplary embodiments, the system can use scans of prior discarded casts of patients to determine the original deformity, stages of correction of the deformity and the final corrected deformity.

In exemplary embodiments, the system can determine the finite element analysis machine learning model based on a point cloud of force vectors determined from prior simulations or finite element analysis for a plurality of patients. For example, the data for the plurality of patients can include the force vectors generated using simulations for a cast in a series of casts, the boundary conditions used to arrive at the force vectors and the correction achieved as evident from the next three-dimensional image of the deformity. In exemplary embodiments, the finite element analysis machine learning model can generate a force vector for a series cast based on the boundary conditions obtained from the machine learning model.

Referring now to FIG. 1A which illustrates a system 100 to capture an image of the deformity according to the present disclosure is provided. The system 100 includes a camera 102 (shown in FIG. 1A as an array of cameras) configured to capture a three dimensional image of a deformity and a plurality of light sources 106. In an exemplary embodiment the system 100 can include a calibration target 110. Examples of the calibration target 110 include checkerboard patterns, socks with or without identification patterns and the like. For example, the calibration target 110 can be a checkerboard pattern that can attached on a flat board that can move relative to the camera 102 to acquire calibration images of the calibration target 110 with various poses relative to the camera 102. In an exemplary embodiment, the system 100 can use a calibration target 110 for subjects where the deformity is kept relatively still. The use of a calibration target with multiple cameras allows the system 100 to capture three-dimensional images and compensate for movement.

In an exemplary embodiment, the camera 102 can be an array of cameras. The system 100 can generate a three-dimensional image of the deformity by stitching all the images from the array of cameras. In an exemplary embodiment, the camera can be a digital camera, or a video camera, an ultrasound imaging system, MRI or a CT scan. The system 100 can compensate for movement of the subject using image processing to obtain an accurate representation of the deformity in three dimensions. In an exemplary embodiment, the system 100 can acquire an image of the deformity from a mobile device such as a phone or tablet camera. The system 100 can receive an image captured from a mobile device that captures the deformity from different angles. The system 100 can then stitch the images together to create a three-dimensional image.

The system 100 can include a computing device 112. The computing device 112 can include a machine learning trainer 114 to generate a machine learning model 116. In an exemplary embodiment, the system 100 can generate a machine learning model based on supervised learning, unsupervised learning or reinforcement learning. The machine learning trainer 114 can analyze a set of training data that includes a classification of the data that the machine learning trainer 114 can use to calibrate its algorithm to identify what lies within a class or is outside a class. For example, a convolutional neural network or deep learning neural network trained on three-dimensional models of club foot can classify a new three-dimensional model based on the trained machine learning model.

For example, the system 100 can generate a machine learning model to determine the boundary conditions for correcting orthopedic deformities. In an exemplary embodiment, the system 100 can receive training data that includes patient profile data of past patients who have had a deformity corrected. The patient profile data can include information about the correction of deformity achieved, the parameters of the original deformity and the parameters of intermediate corrections achieved, for example, with respect to clubfoot the prior patient data may be based on the Ponseti method. The system 100 can use the machine learning trainer 114 to generate a machine learning model 116. In an exemplary embodiment, machine learning models analyze data from a plurality of prior patients to identify mean shapes and shape variations and determine boundary conditions to classify a new three-dimensional surface model of a deformity as falling within the boundary. The system 100 can use the machine learning model to fit the three-dimensional image of the deformity based on machine learning. The system 100 can then determine the boundary conditions such as the desired correction angles and the like.

For example, the system 100 can train the machine learning model based on prior patient data for a plurality of patients such an original three-dimensional image of the deformity, images of intermediate stages of correction of the deformity and the final image of the corrected deformity. In exemplary embodiments, the system can use three dimensional scans of prior discarded casts of patients to determine the original deformity, stages of correction of the deformity and the final corrected deformity. The system 100 can use the prior discarded casts to approximate the deformity at each stage of the correction process where 3 dimensional three-dimensional images of the foot are not available.

Figure 1B:
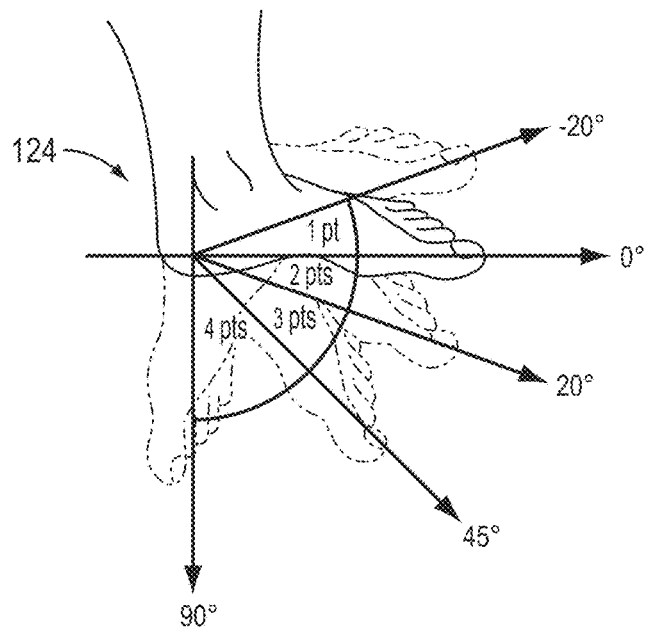
FIG. 1B is an illustration of the corrective vector forces for correcting an orthopedic deformity in accordance with various embodiments taught herein.
Figure 1B:
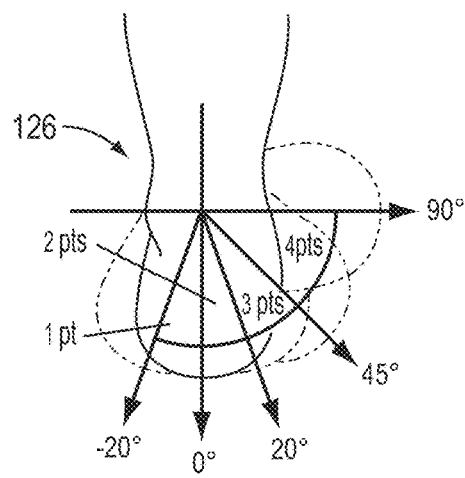
Figure 1B:
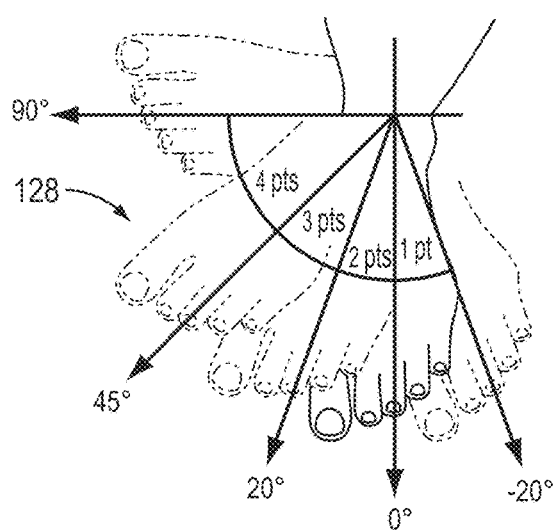
Figure 1B:
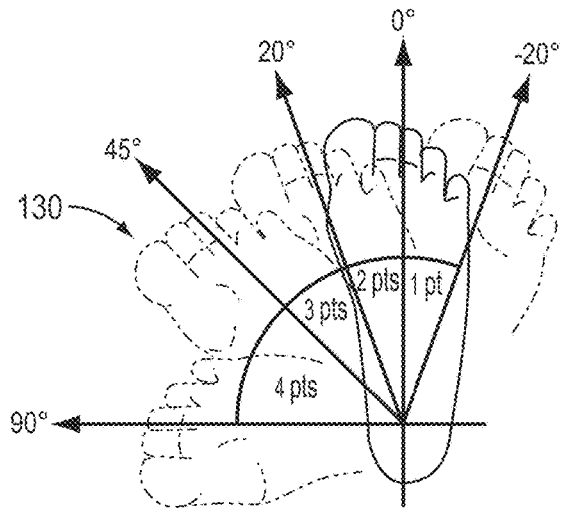

In an exemplary embodiment, the system 100 can generate training data for the machine learning model based on modelling and analysis software such as ANSYS. Modelling and simulation software can be used to deform a 3D three-dimensional CAD model of a normal foot into a plurality of virtually generated CAD models (e.g., 500 models), for example, clubfoot CAD models, with different degrees and angles of deformity potentially seen during the correction sequence. In an embodiment, system 100 can use supervised learning and the system 100 can receive inputs from an orthopedic surgeon (e.g., pediatric orthopedic surgeon) to review the models for accuracy. The system 100 can export the CAD models as point cloud models for anatomical classification/labeling of the generated models for the machine learning model. The system 100 can use the point cloud model of the foot to identify the severity of the clubfoot deformity by determining the amount of deviation of the foot with respect to normal pose in four different directions as shown in FIG. 1B. FIG. 1B illustrates the deformities in clubfoot such as the equinus deformity 124, the varus deformity 126, the calcancopedal derotation 128 and the horizontal plane deformity relative to hindfoot 130. The system 100 can capture the variation in these deformities using the camera 102. In an exemplary embodiment, the machine learning model can be evolved to improve the accuracy of the model over time.

The system 100 can use a deep learning method such as a PointNet to process the point cloud models. PointNet is an open source platform for classification of point cloud models. Since the point cloud model is randomly oriented, they use a bounding box that fits into the model, and normalizes the point cloud to always align the point cloud model in a certain direction before feeding it into the deep learning network as input datasets. The system 100 can use PointNet to classify different stages of an orthopedic skeletal deformity, for example, clubfoot deformity. In an exemplary embodiment, the system 100 can use the point cloud CAD models generated using simulation software to train a deep learning network to objectively classify and label each patient's unique foot deformity compared to a normal foot. The system 100 can then train the network to predict the cast series for each subject patient in this study. The system 100 can use supervised learning based on inputs obtained by presenting an orthopedic skeletal deformity model, for example, a clubfoot model, to one or more orthopedic surgeons. In an exemplary embodiment, the models can be presented with a selection of candidate foot correction models (e.g., out of five hundred foot models) that is the next in the correction series based on the Ponseti method. The system 100 can then receive inputs from the doctors on a consensus basis and select the next correction phase out of the selection of candidate foot models (e.g., 10 models). Over the course of multiple rounds of selection (e.g., 500 rounds) the system 100 trains the deep learning network to search the training dataset and output the subsequent cast for deformity correction.

In an exemplary embodiment, the system 100 can generate an STL file for three-dimensional printing using a three-dimensional printer 122.

Figure 2:
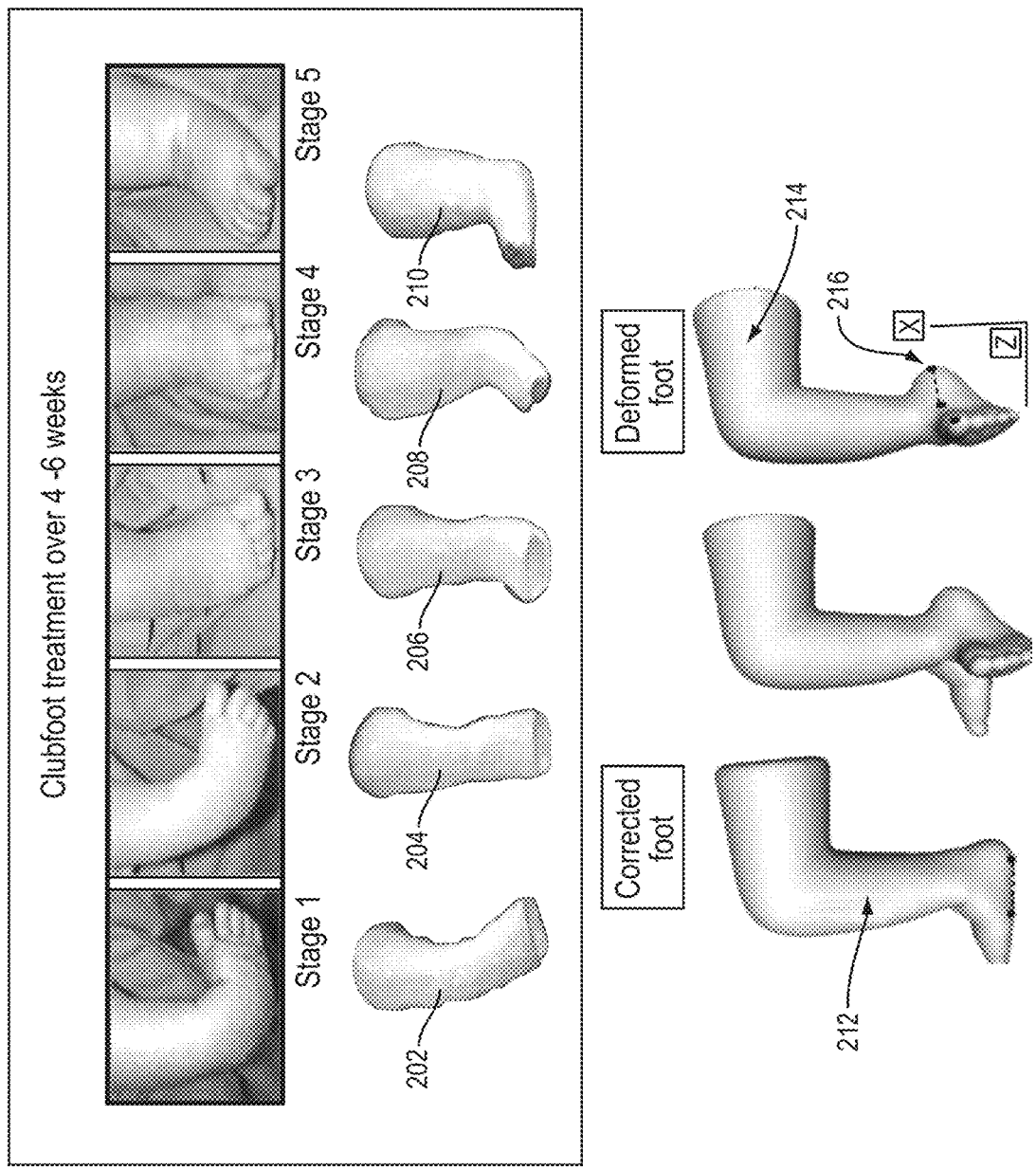
FIG. 2 is an illustration of a series of casts generated to correct the orthopedic deformity in accordance with various embodiments taught herein.

Referring to FIG. 2, the system 100 can generate a cast or a series of casts as shown in FIG. 2 to correct the orthopedic deformity. In an exemplary embodiment the system 100 can generate a cast or a series of casts that can be three-dimensional printed. The system 100 determines a force vector or a set of force vectors to correct the orthopedic deformity based on the boundary conditions and based on the three-dimensional imagery of the deformity. In an exemplary embodiment, the boundary condition can be the desired corrected angles for the deformity. In an exemplary embodiment, the system 100 can determine the shape and geometry of a cast or a series of casts 202-210 that exert the determined force vector or set of force vectors that are tailored to the patient. In an exemplary embodiment, the system 100 can determine the force vectors for the series of casts 202-210 to correct the deformed foot 214 with three-dimensional deformities shown along the x, y and z axis to arrive at the corrected foot 212. In an exemplary embodiment, the system 100 selects the force vector or set of force vectors is selected such that the right areas 216 that are structurally designed in normal foot of children to distribute the load when walking is in the same plane and perform the load bearing function once corrected.

It can be appreciated that, depending on the baseline anatomical shape and arrangement and an anatomical rearrangement goal, or target, an appropriate serial casting strategy can be developed. For instance, not all patients may need the same number of casts. In fact, it may be that a patient requires fewer casts as deformities to the internal anatomy of the foot may be less severe. In other cases, the deformity to the underlying anatomy may be significant and more casts may be prescribed. Being able to combine this internal information, however, with exterior data of the surface of the foot allows for generation of three-dimensional printed 'corrective' casts that are patient-specific.

Figure 3A:
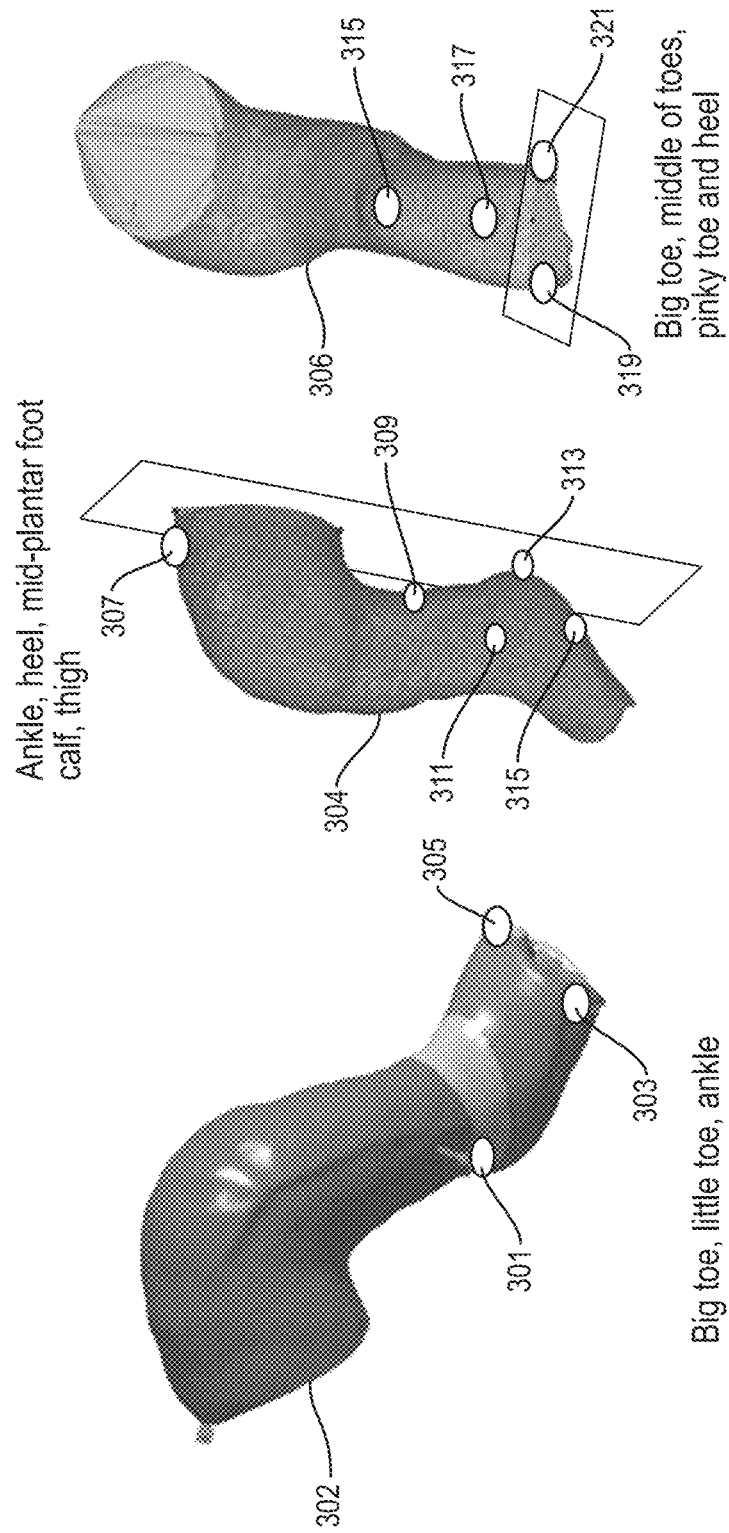
FIGS. 3A and 3B are illustrations of selecting reference points and determining the planes for correction in accordance with various embodiments taught herein.
Figure 3B:
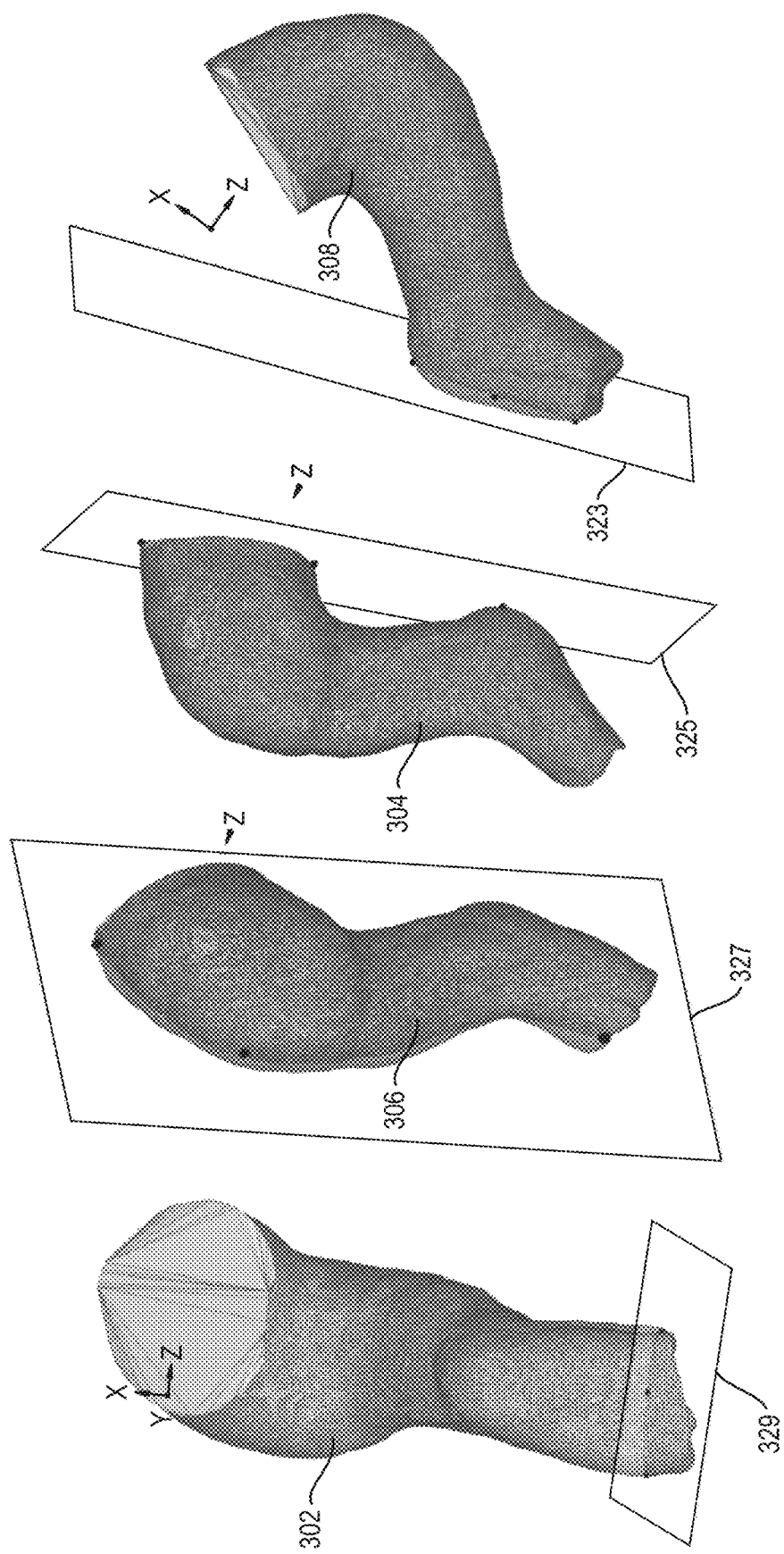
Figure 3C:
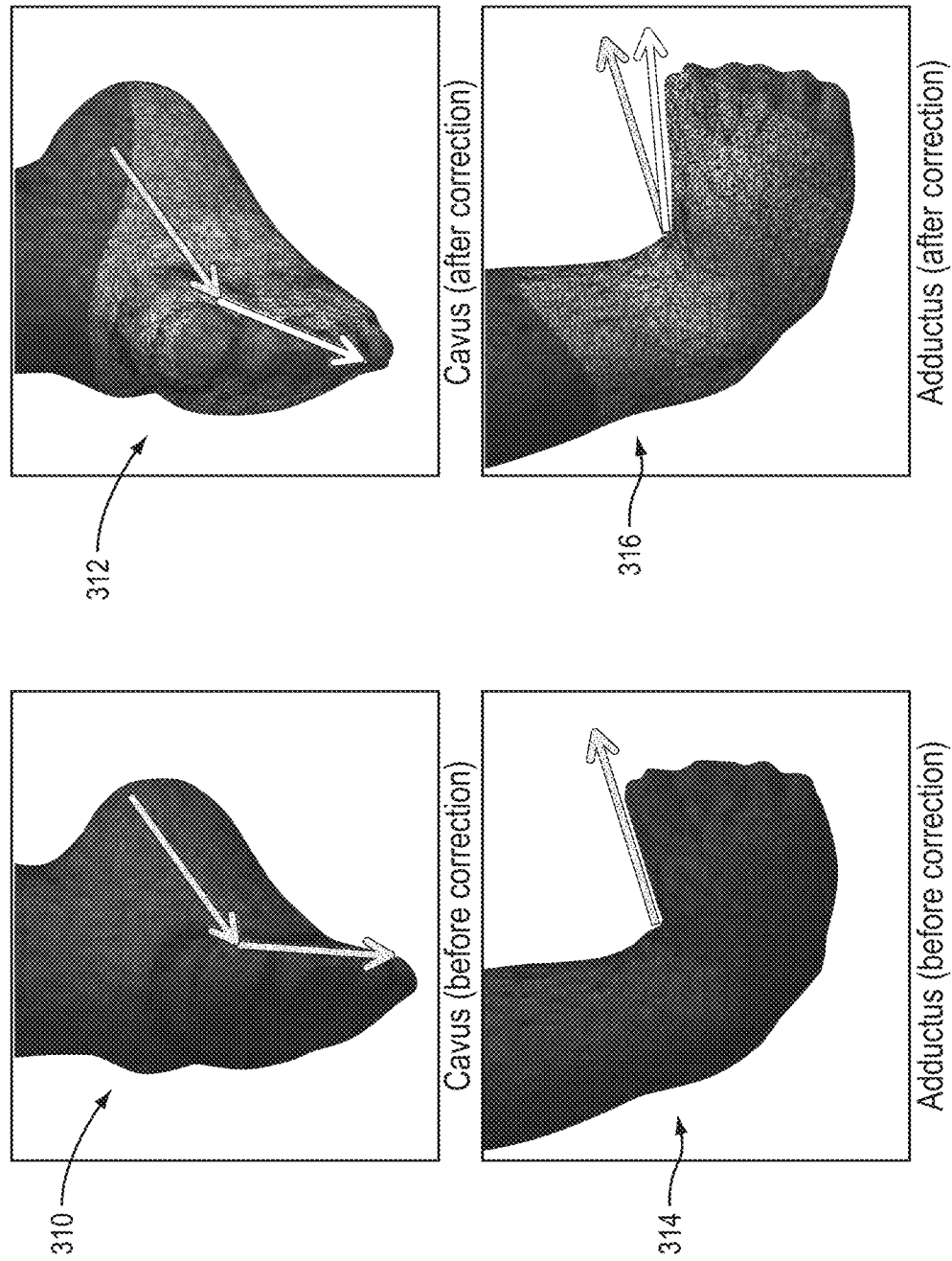
FIGS. 3C, 3D, and 3E are illustrations of corrections of deformities using finite element analysis in accordance with various embodiments taught herein.
Figure 3D:
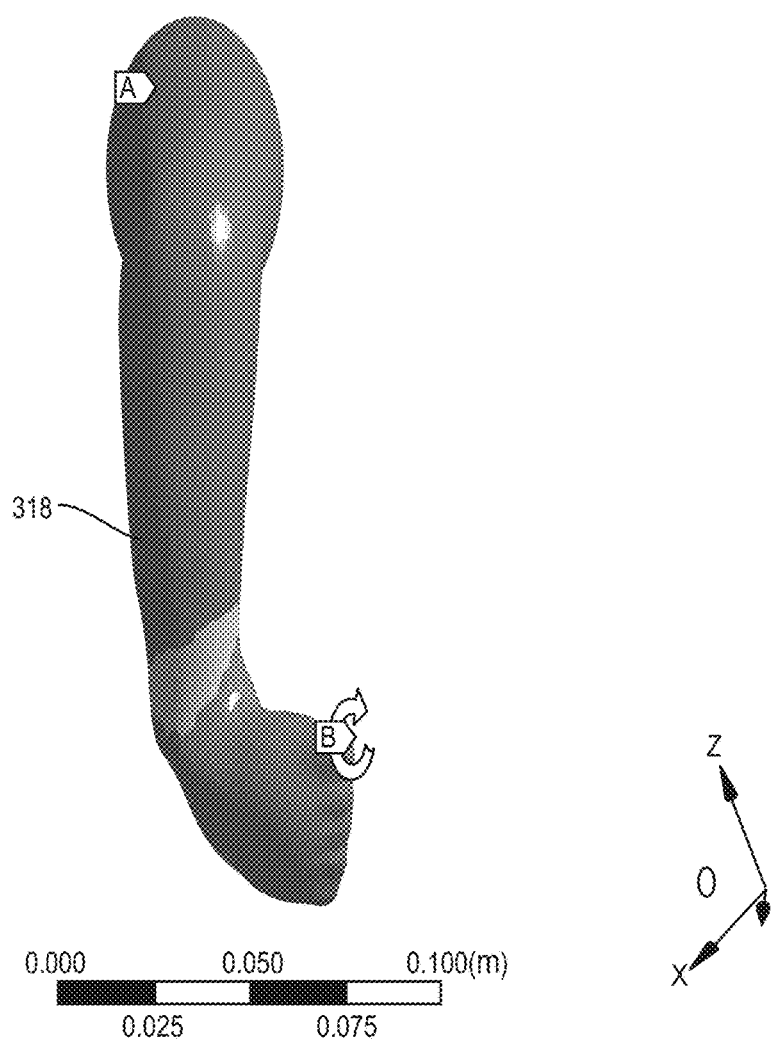
Figure 3E:
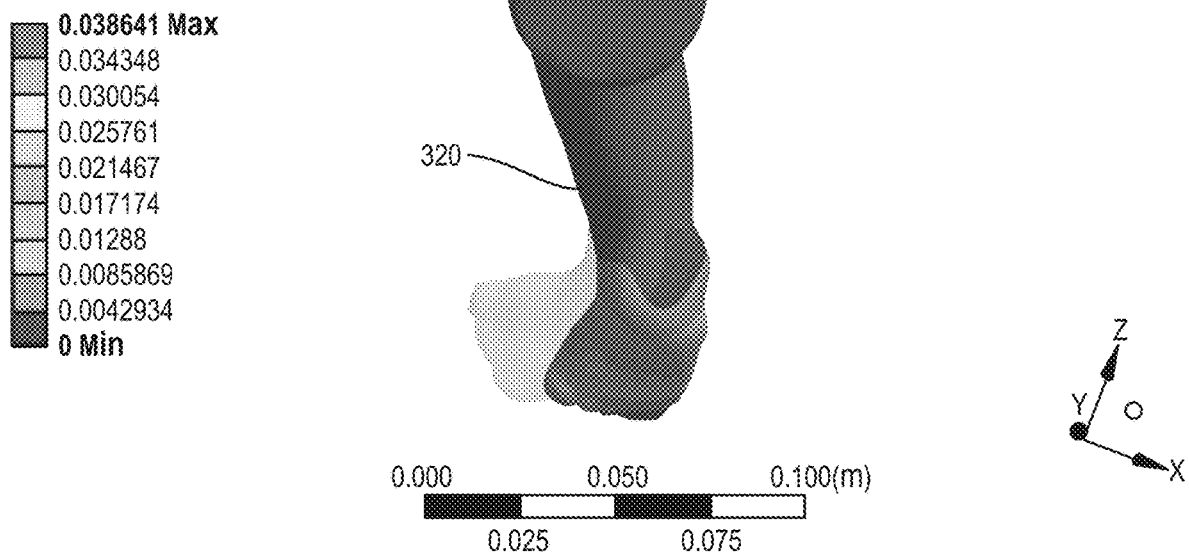
Figure 3E:
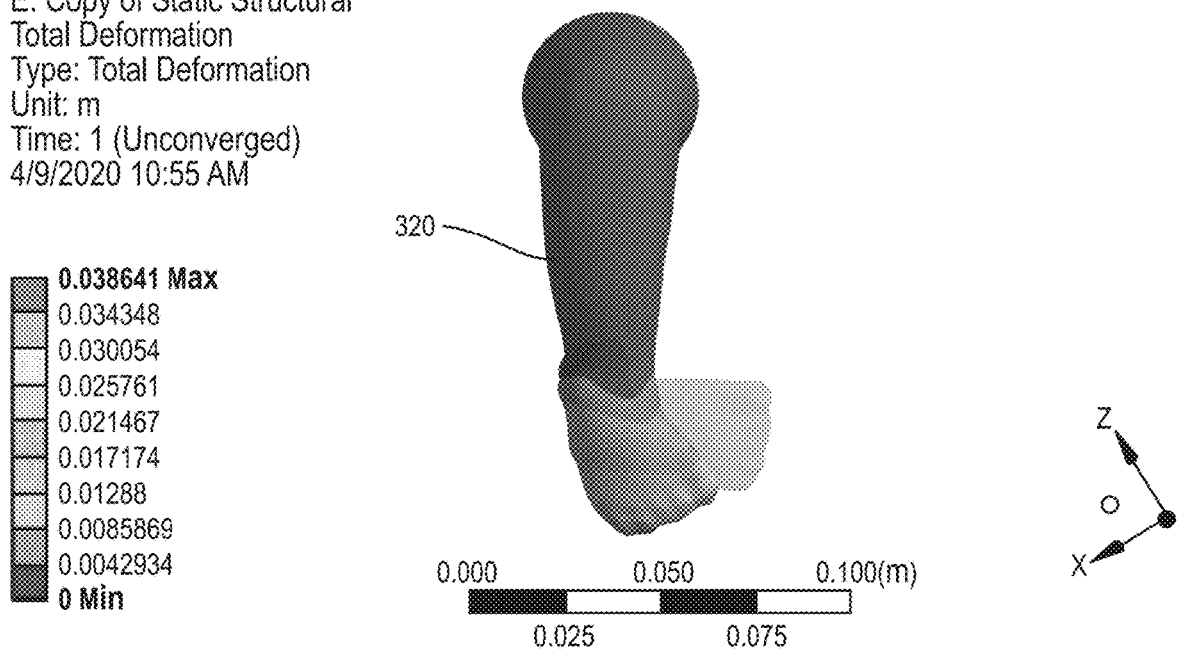

Referring now to FIGS. 3A, 3B, 3C, and 3D the system 100 can determine the reference points for generating the corrective plane. FIGS. 3A and 3B illustrates the reference points for generating the corrective planes. FIG. 3C illustrates before correction cavus image 310 and after correction cavus image 312 generated by the system 100 using finite element analysis. FIG. 3C also illustrates the before correction Adductus image 314 and the after correction Adductus image 316 generated by the system 100 using finite element analysis. FIG. 3D and FIG. 3E illustrates the before correction Varus image 318 and the after correction Varus image 320 (from two different points of view) generated by the system 100 using finite element analysis.

In an exemplary embodiment, the system 100 can determine the reference points for an adductus deformity based on the big toe 305, little toe 303, and ankle 301 as shown in a three-dimensional image of the adductus deformity 302 in FIG. 3A. In an exemplary embodiment, the system 100 can use these reference points to generate the reference plane 323 as shown in FIG. 3B. The system 100 can use the reference plane 323 to determine the force vectors to correct the adductus deformity 314, 316 as shown in FIG. 3C.

The system 100 can determine the reference points for correcting an equinus deformity based on the ankle 311, heel 313, mid plantar of foot 315, and thigh 307 as shown in a three-dimensional image of the equinus deformity 304 as shown in FIG. 3A. In an exemplary embodiment, the system 100 can use these reference points to generate the reference plane 325 to determine the force vectors to correct the equinus deformity as shown in FIG. 3B. The system 100 can then determine the force vector or set of force vectors to correct an equinus deformity based on the reference plane 327.

The system 100 can determine the reference points for correcting a cavus deformity based on the big toe 319, middle of toes 317, pinky toe 321 and heal 315 as shown in a three-dimensional image of the cavus deformity 306 in FIG. 3A. The system 100 can determine the reference plane 323 based on these reference points as shown in FIG. 3B. The system 100 can then determine the force vector or set of force vectors to correct the cavus deformity 310, 312 as shown in FIG. 3C.

The corresponding FIG. 3B illustrates identification of four different planes using these reference points shown in FIG. 3A. In an exemplary embodiment system 100 can determine these reference points using image processing algorithm or a machine learning algorithm that recognizes features of the limb. In an exemplary embodiment, the machine learning model can be trained on deformed foot to identify these features.

Figure 4A:
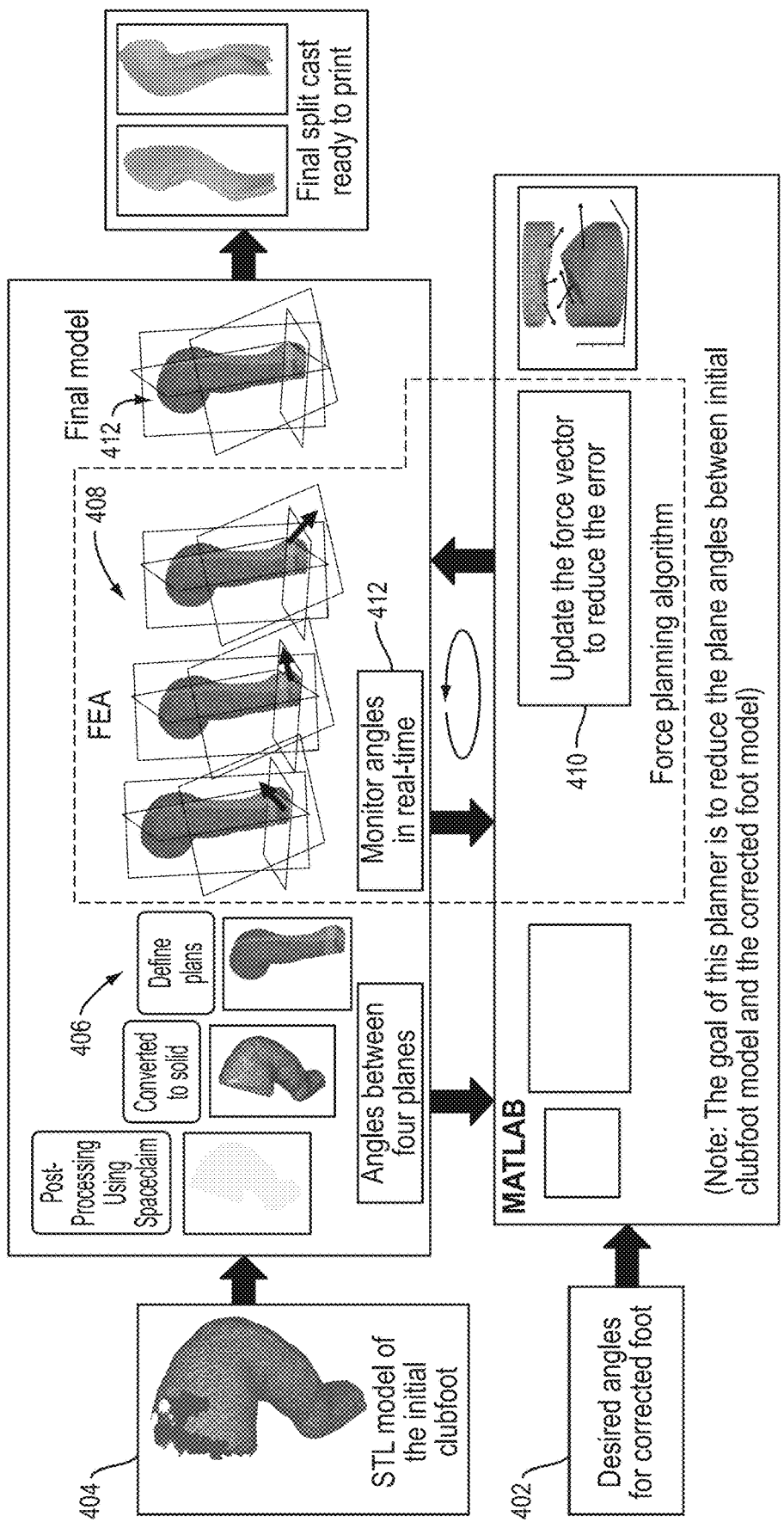
FIG. 4A is an illustration of the process of determining a next cast in a series of casts based on the three-dimensional image of the deformity and the boundary conditions in accordance with various embodiments taught herein.
Figure 4B:
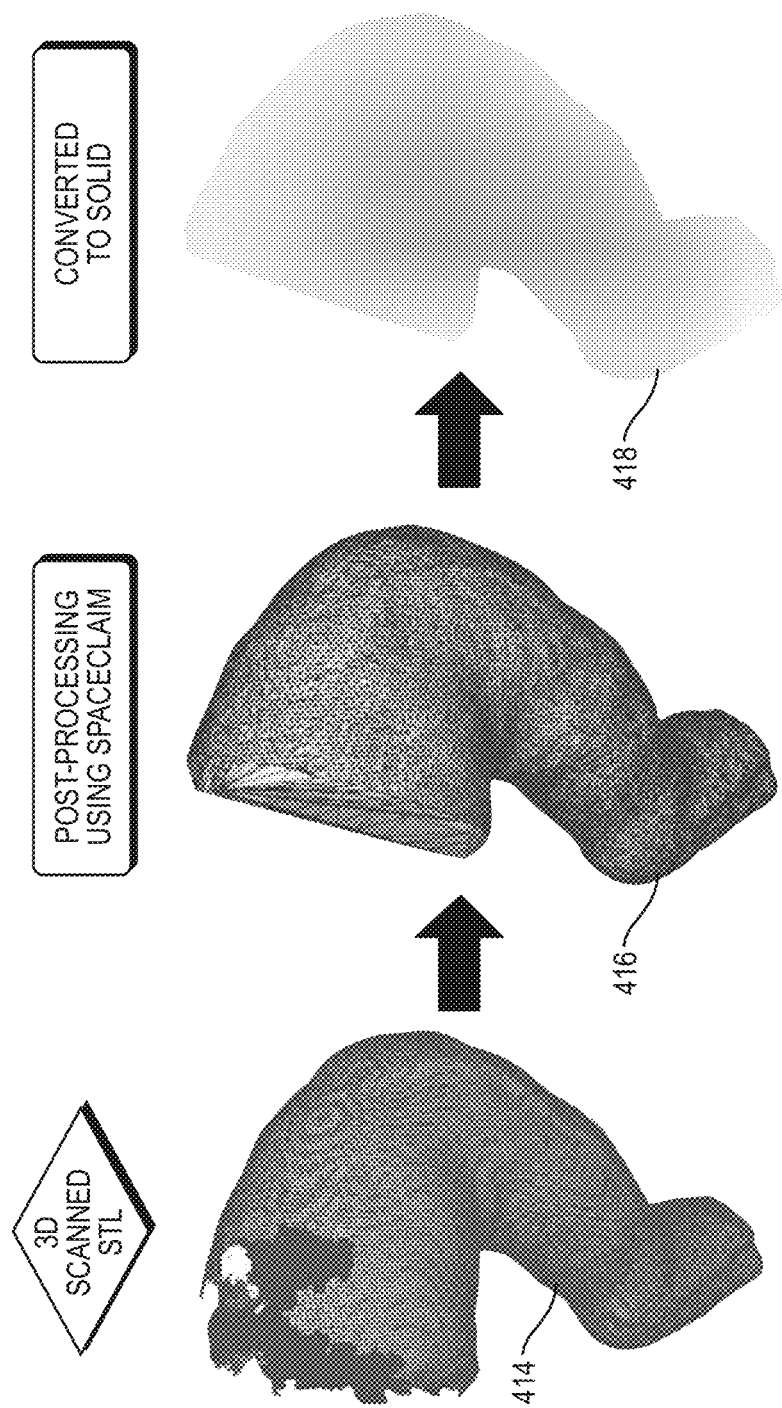
FIG. 4B is an illustration of the post-processing in accordance with the various embodiments taught herein.
Figure 4C:
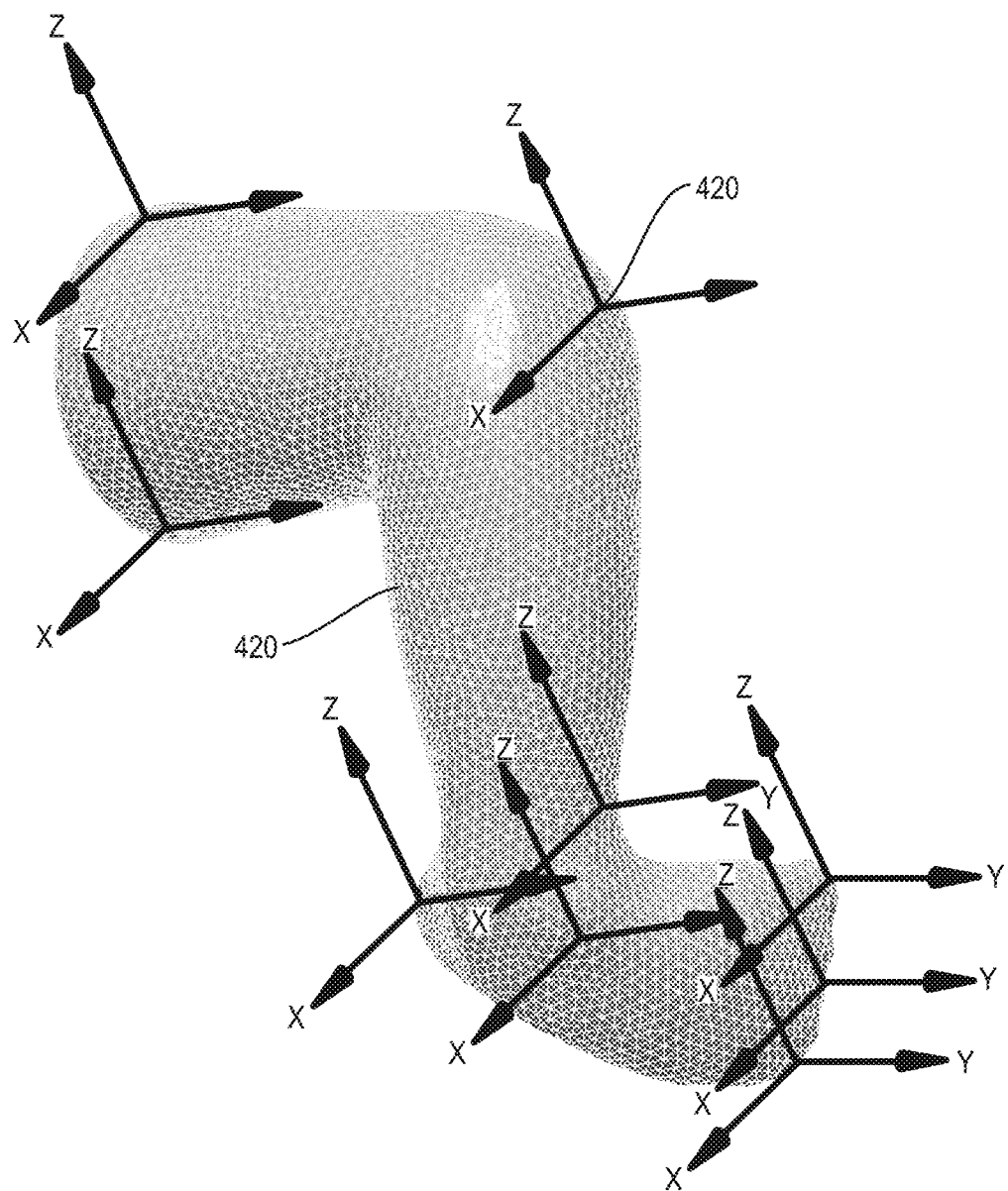
FIG. 4C is an illustration of force vectors at selected reference points in accordance with the various embodiments taught herein.

With reference to FIGS. 4A, 4B and 4C, the system 100 can be configured to determine the boundary conditions of the deformity based on a machine learning model. In an exemplary embodiment, the boundary conditions of the deformity can be the desired angles for corrected foot 402. FIG. 4A illustrates the process of generating a final model of force vectors for correcting a deformity based on the boundary conditions and the 3d model of the deformity. FIG. 4B illustrates the process of generating a solid model based on 3d scans. FIG. 4C illustrates the force vectors at the reference points determined by the system 100 in accordance with an exemplary embodiment described herein.

The system 100 can obtain a three-dimensional image or data 404 of the deformity. In exemplary embodiments, the system 100 can generate a three-dimensional model of the deformity either as a solid object or as a point cloud. FIG. 4B illustrates a method of generating a three-dimensional solid object in a modelling software based on the images of the foot. The system 100 can convert the three-dimensional scan images of the deformity into an STL file 414. The system 100 can then post-process the STL file 414 to fill in any missing information using a post-processing tool (e.g., Spaceclaim). The system 100 can then convert the post-processed file into a solid three-dimensional object in the modelling software for further analysis.

Returning to FIG. 4A, the system 100 can determine multiple separate planes for the deformity as shown in 406 to serve as a reference between the position of the deformity and the expected or normal mean position of the limb or other appendage. The system 100 can select the number of planes based on the geometry of the deformity, the degrees of freedom of the deformity, the deviation of the deformity from a statistical normal limb or appendage and the like. In an exemplary embodiment, the system 100 can determine the reference points as described above with reference to FIG. 3A-3E. In an exemplary embodiment, the system 100 can select four different planes based on a machine learning model for club foot. In another example, the four planes can be selected with inputs from a doctor. The system 100 can use the machine learning trainer 114 to determine a four plane machine learning model that identifies the appropriate planes to use for correction.

For example, the machine learning trainer 114 can use data from a plurality of prior patients that includes planes that were selected for correction for the patients compared and the geometry of the deformity and the outcome of the corrective effort. The system 100 can then fit the three-dimensional data 404 of the deformity based on the trained four plane machine learning model. Once the four planes are identified the system 100 can use finite element analysis 408 to determine the force vectors for correcting the deformity in each plane.

In an exemplary embodiment, the system 100 can determine the force vectors at the reference points as illustrated in FIG. 4A and FIG. 4C using finite element analysis. The system 100 can determine the force vectors 422 as shown in FIG. 4C at the reference points for correcting the deformity. In an exemplary embodiment, the system 100 can apply a corrective force and determine the predicted correction such as the predicted angles for the corrected foot based on the applied force. The system 100 can then compare it with the boundary conditions such as desired angles for the corrected foot. The system 100 can iterate or simulate 410 for various force corrections then update the force vectors to reduce the error or minimize the error.

In an exemplary embodiment, the system 100 can use the boundary conditions 402 and the angle between the four planes and the boundary conditions 402 to determine the force vectors required during finite element analysis for correcting the deformity in each plane and generating for the next cast in the series of casts. In an exemplary embodiment the system 100 can determine the angle between the four planes using the modelling tools (e.g., Ansys, Matlab or both). Although the FIG. 4A illustrates the use of two modelling tools (e.g., Ansys and Matlab), to perform the various methods, in an exemplary embodiment the system 100 can use one or more modelling tools to perform the various methods.

For example, the system 100 can use the boundary conditions to iterate through a series of force vectors to minimize the error between the boundary condition and the results of applying a particular force vector in a particular plane. The system 100 can run a series of simulations using a trial correction and then determine the probable corrected deformity. The system 100 can as shown in the FIG. 4A iterates over a number of simulations until a force vector or a set of force vectors for the next series cast such as final model 412 is obtained. The system can determine the force vector or set of force vectors with the minimum deviation from the boundary condition using the iterative process. In an exemplary embodiment when the angle between the boundary conditions 402 and the probable corrected deformity is minimal the error is minimum. In an exemplary embodiment the system 100 can track the angle between the boundary condition and the predicted or estimated corrected plane if a force vector or set of force vectors is applied for each simulation in real-time 412.

In an exemplary embodiment, the system 100 can generate data for split casts based on the final model 412. In an exemplary embodiment, the split cast can include a portion that is not changed during at least a part of the series of casts and a portion that is updated during the next cast in the series of casts.

In exemplary embodiments, the system 100 can use the machine learning trainer 114 to determine the finite element analysis machine learning model. The finite element analysis machine learning model can be based on a point cloud of force vectors determined from prior simulations for a plurality of prior patients. For example, the data for the plurality of prior patients can include the force vectors generated using simulations for a next cast in a series of casts, the boundary conditions used to arrive at the force vectors and the correction achieved as evident from the subsequent three-dimensional image of the deformity after it was corrected with the cast can be used to train the finite element analysis machine learning model. In exemplary embodiments, the finite element analysis machine learning model can generate a force vector or a set of force vectors for a cast or a series of casts based on the boundary conditions given manually or obtained from the finite element analysis machine learning model.

The system 100 can run supervised learning, unsupervised learning, reinforcement learning algorithms or any combination thereof. Examples of machine learning algorithms that can be implemented via the computing device 112 can include, but are not limited to Linear Regression, Logical Regression, Decision Tree, Support Vector Machine, Naïve Bayes, k-Nearest Neighbors, k-Means, Random Forest, Dimensionality Reduction algorithms such as GBM, XGBoost, LightGBM and CatBoost.

Examples of supervised learning algorithms that can be used in the computing device 112 can include regression, decision tree, random forest, k-Nearest Neighbors, Support Vector Machine, and Logic Regression. Examples of unsupervised learning algorithms that may be used in the computing device 112 include apriori algorithm and k-means. Examples of reinforcement learning algorithms that may be used in computing device 112 includes a Markov decision process.

Figure 5:
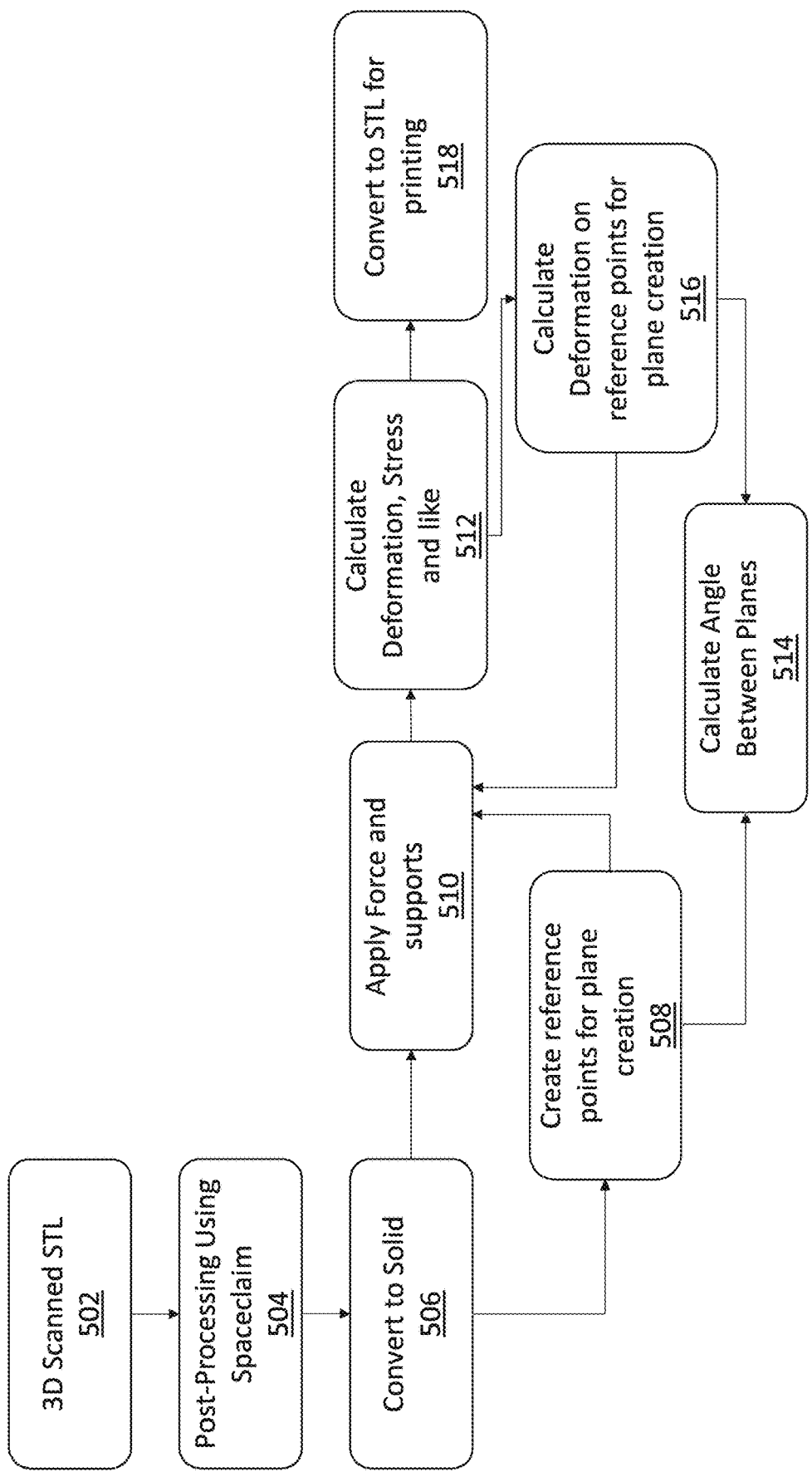
FIG. 5 is an illustration a finite element analysis modelling in accordance with various embodiments taught herein.

Referring to FIG. 5, the system 100 can apply finite element analysis manually. At step 502 the system 100 can generate a three-dimensional scanned stereolighography (STL) file based on the three-dimensional image from the camera 102. At step 504 the STL file can be post processed to clean up any irregularities. For example, the system 100 can remove any imperfections in the STL file such as from motion during capture of the three-dimensional image using image processing algorithms. At step 506 the system 100 can convert the three-dimensional image to a three-dimensional solid model. For example, the system 100 can use the multiple points present in the STL file and generate a solid shape of the deformity that are connected using extrapolations to generate a surface instead of multiple discrete points. At step 508 the system 100 can create reference points for generating the planes for finite element analysis of the force vector or set of force vectors to be applied to the deformity to correct the deformity. In an exemplary embodiment, the system 100 can receive a selection of reference points for generating a correction plane from the doctor. In another example, a machine learning algorithm can select the reference points based on a trained machine learning model as described herein above. At step 510 the system 100 can simulate the application of the force vector to the deformity and the effect of the force vector on the points of support for the deformity. At step 512 the system 100 can calculate the deformation and the stresses when the force vector is applied. For example, the system 100 can determine the deformation of the deformity and the stresses on the deformity when the force vector or set of force vectors is applied via a cast. At step 516 the system can calculate the deformation on the reference points for plane creation. For example, the system 100 can determine the deformation on the chosen reference points in the deformity to determine the effect of the force vectors on the deformity. At step 514 the system 100 can calculate the angle between the planes of the selected reference place and the desired boundary condition 502. And at step 518 the system can convert the generated final model data into a next cast in the series of casts. The system 100 can convert the final model into an STL file for three-dimensional printing.

Figure 6A:
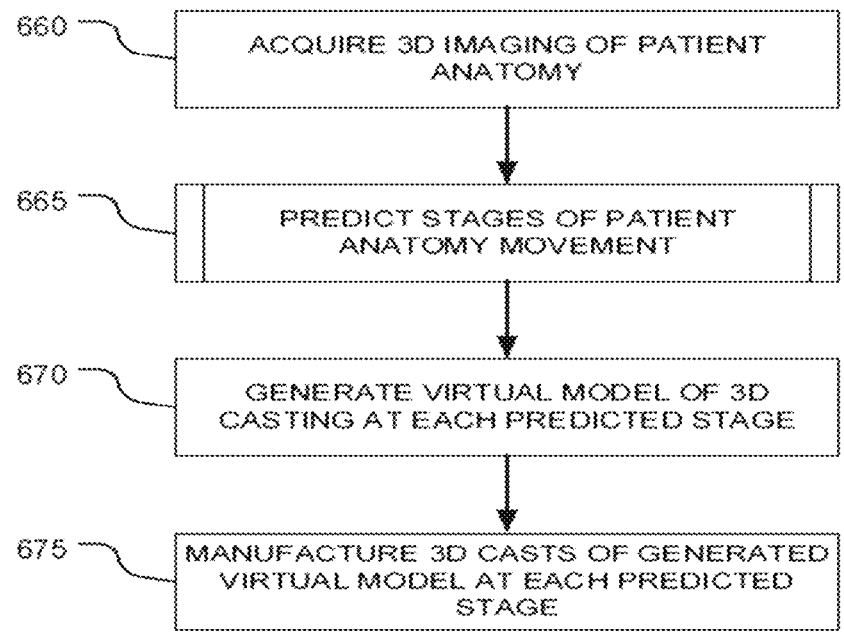
FIG. 6A illustrates a flowchart for image acquisition of the deformity and generation of a predicted virtual casting model in accordance with various embodiments taught herein.

Referring now to FIG. 6A, the method of the present disclosure will now be described with reference to the flowchart. At step 660 of process 655, three-dimensional images of the deformity can be acquired. In an embodiment, the three-dimensional images of the deformity can be acquired by a mobile device of a parent. The three-dimensional imaging can include depth mapping of the foot of the patient. In an embodiment, the three-dimensional imaging can include ultrasound for the determination of internal biological structures of the foot. In an exemplary embodiment, the combination of the two above-described three-dimensional imaging modalities allows for improved cast planning by considering the internal structures in addition to the outward appearance.

At sub process 665 of process 655, and based upon the acquired three-dimensional images of the patient anatomy, casting stages of patient anatomy movement can be predicted. The casting stages can be predicted via the force vector modeling described herein above. In one instance, this prediction can include computer predictive modeling and finite element analysis of the foot wherein stresses, deformations of the structures of the foot or both are considered from one stage to the next. Sub process 665 will be further described with reference to FIG. 6B. At step 670 of process 655, virtual models of three-dimensional casts can be generated for anticipated patient anatomy movements at each predicted stage. Such virtual models of three-dimensional casts can allow for visualization and modification according to real-world constraints. At step 675 of process 650, three-dimensional casts, similar to that of FIG. 5, can be generated for each virtual model at each predicted stage of patient anatomy movement.

Figure 6B:
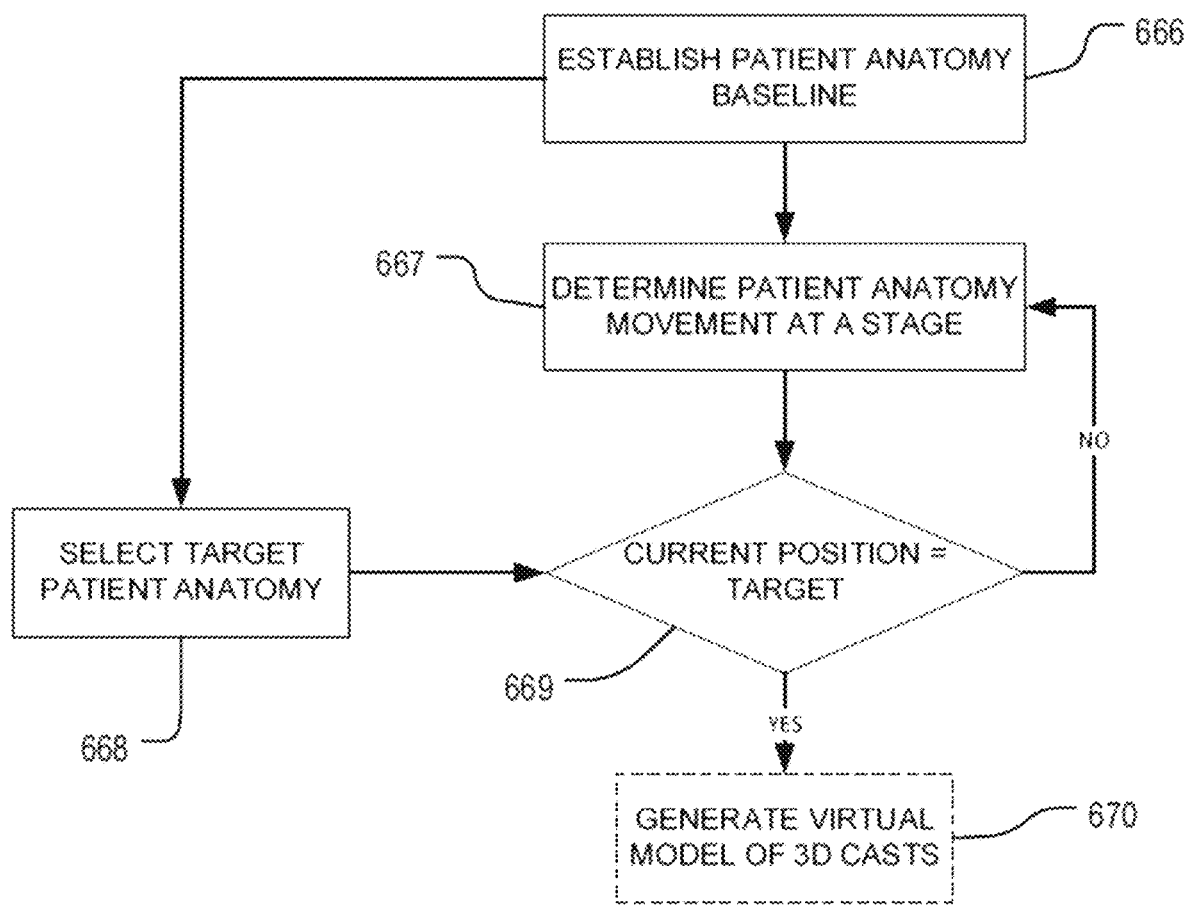
FIG. 6B illustrates a flow chart for determining the number of stages and trajectory of the predicted movement in accordance with various embodiments taught herein.

With reference to FIG. 6B, sub process 665 of process 655 includes determining the number of stages and trajectory of each predicted stage of movement. At step 666 of sub process 665, a baseline patient 5 anatomy can be established according to the acquired images of the patient anatomy. Accordingly, at step 668 of sub process 665, a target patient anatomy can be selected, the target being an end goal shape of the structure of the foot.

At step 667 of sub process 665, the patient anatomy movement at each stage can be determined. This determination can include movements of structures of the foot. In an embodiment, such movements can be determined in the context of the Ponseti stages and include, for instance, performing specific angular rotations at specific stages. In an embodiment, such movements can be optimized at each stage such that maximum movement is achieved without creating undue mechanical and/or biological stresses. For instances, each stage may be determined such that von Mises stress, for instance, remain below a threshold value.

At step 669 of sub process 665, the current position of the patient anatomy can be compared with the target patient anatomy position from step 668. If the two values are equal, for instance, only a single stage of casting may be required and the determined patient anatomy movement can be used to generate a virtual model of a necessary three-dimensional cast at step 670. If, however, the current position and the target patient anatomy do not match, a successive stage of patient anatomy movement is required and the sub process 665 returns to step 667.

According to an embodiment, in this way, the number of stages, or cast, required to be fitted to a patient is dependent upon the severity of the deformity and the ability to move the patient anatomy at each stage. In the case of clubfoot, this can mean the difference of manufacturing four casts in one instance and six casts in another, thereby allowing each patient to receive only the minimum necessary number of casts.

According to an embodiment, the above described method of FIG. 6A and FIG. 6B can be performed with only external features gathered via, for instance, depth mapping data. External features can be processed similarly to Schoenecker, et al., Systems and methods for serial treatment of a muscular-skeletal deformity, U.S. Patent Application Publication No. US2017/0091411 A1, incorporated herein by reference.

According to an embodiment, the external features can be applied to a machine learning algorithm in order to generate patient anatomy predictions without need for ultrasound imaging. For instance, a library of corresponding images of a foot may be stored.

The corresponding images can include images of the external features of the foot and corresponding images of the internal features of the foot. In this way, the machine learning algorithm, a convolutional neural network in exemplary embodiment, can be trained to correlate external features with internal features. Therefore, when provided with an external feature of an unknown foot, the machine learning algorithm can generate a corresponding internal feature structure that can be used in determining patient anatomy movements during stage planning. The library of corresponding images can be a corpus of patient data acquired from patients of a similar diagnosis and healthy patients.

Figure 7:
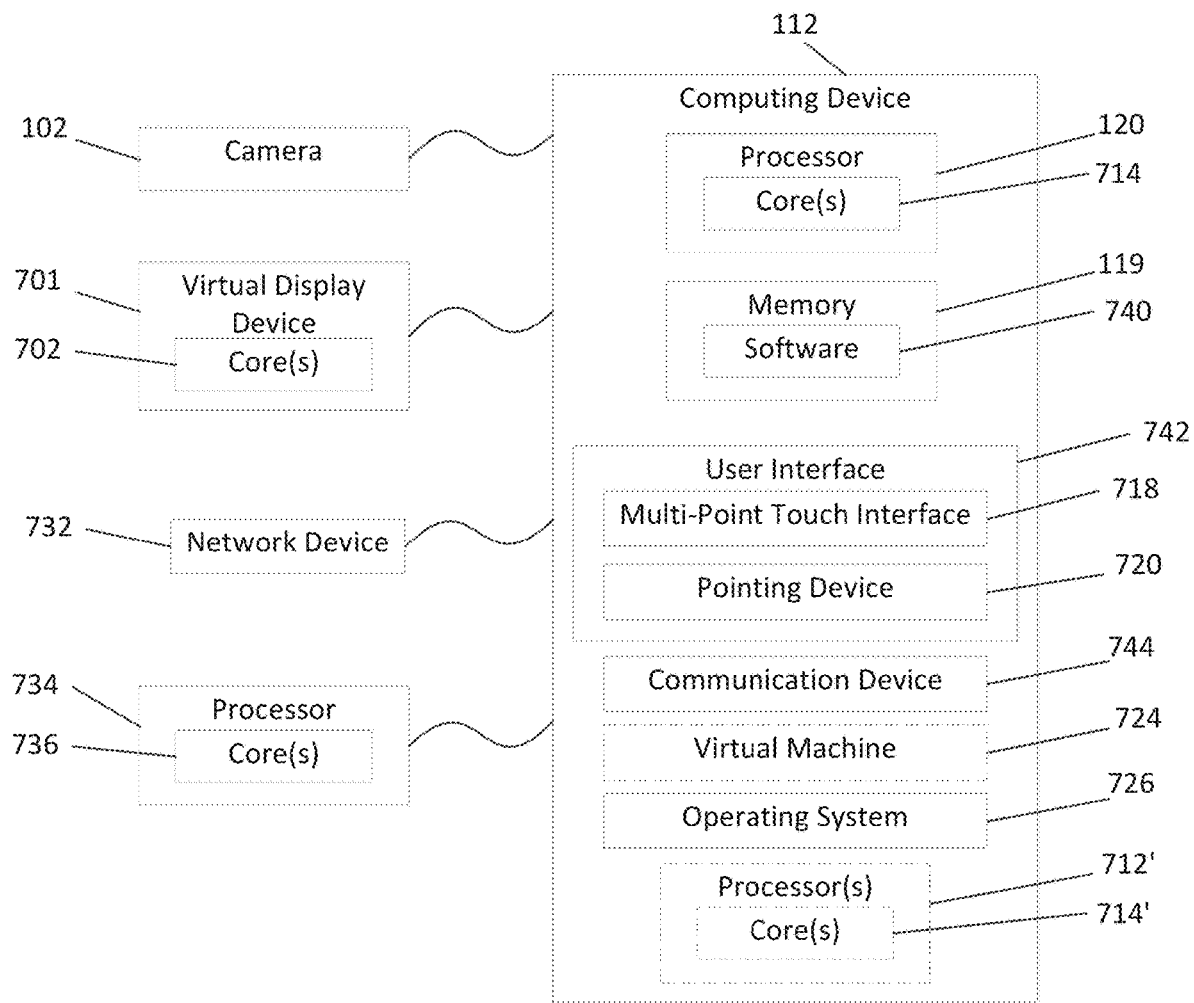
FIG. 7 illustrates an exemplary computing system for determining the force vectors for correcting a deformity in accordance with various embodiments taught herein.

FIG. 7 is a block diagram of an exemplary embodiment of computing device 112 in accordance with embodiments of the present disclosure. The computing device 112 can include one or more non-transitory computer-readable media for storing one or more computer-executable instructions or software for implementing exemplary embodiments. The non-transitory computer-readable media can include, but are not limited to, one or more types of hardware memory, non-transitory tangible media (for example, one or more magnetic storage disks, one or more optical disks, one or more flash drives), and the like. For example, memory 119 included in the computing device 112 can store computer-readable and computer-executable instructions or software for performing the operations disclosed herein. For example, the memory 119 can store a software application 640 which is configured to perform several of the disclosed operations (e.g., the pre-training platform for determining the co-occurrence matrix, the training platform for determining the word vectors and the topic determination platform for determining the plurality of topics and the representative noun). The computing device 610 can also include configurable, programmable processor 120 or both and an associated core(s) 614, and optionally, one or more additional configurable, programmable processing devices or both, e.g., processor(s) 612' and associated core(s) 614' (for example, in the case of computational devices having multiple processors/cores), for executing computer-readable and computer-executable instructions or software application 640 stored in the memory 119 and other programs for controlling system hardware. Processor 120 and processor(s) 612' can each be a single-core processor or multiple core (614 and 614') processor.

Virtualization can be employed in the computing device 610 so that infrastructure and resources in the computing device can be shared dynamically. A virtual machine 624 can be provided to handle a process running on multiple processors so that the process appears to be using only one computing resource rather than multiple computing resources. Multiple virtual machines can also be used with one processor.

Memory 119 can include a computational device memory or random access memory, such as DRAM, SRAM, EDO RAM, and the like. Memory 119 can include other types of memory as well, or combinations thereof.

A user can interact with the computing device 710 (shown in FIG. 1 as 112) through a visual display device 701, such as a computer monitor, which can display one or more user interfaces 742 that can be provided in accordance with exemplary embodiments. The computing device 710 can include other I/O devices for receiving input from a user, for example, a keyboard or any suitable multi-point touch interface 718, a pointing device 720 (e.g., a mouse). The keyboard and the pointing device 720 can be coupled to the visual display device 701. The computing device 710 can include other suitable conventional I/O peripherals.

The computing device 710 can also include one or more storage devices such as a hard-drive, CD-ROM, or other computer readable media, for storing data and computer-readable instructions, software that perform operations disclosed herein or both. Exemplary storage device 734 can also store one or more databases for storing any suitable information required to implement exemplary embodiments. The databases can be updated manually or automatically at any suitable time to add, delete, and update one or more items in the databases.

The computing device 710 can include a communication device 744 configured to interface via one or more network devices 732 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The communication device 744 can include a built-in network adapter, network interface card, PCMCIA network card, card bus network adapter, wireless network adapter, USB network adapter, modem, radio frequency transceiver, or any other device suitable for interfacing the computing device 710 to any type of network capable of communication and performing the operations described herein. Moreover, the computing device 710 can be any computational device, such as a workstation, desktop computer, server, laptop, handheld computer, tablet computer, or other form of computing or telecommunications device that is capable of communication and that has sufficient processor power and memory capacity to perform the operations described herein.

The computing device 710 can run any operating system 726, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 726 can be run in native mode or emulated mode. In an exemplary embodiment, the operating system 726 can be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further still, other aspects, functions and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts and that the steps in the exemplary flowcharts may be performed in a different order than the order shown in the illustrative flowcharts.

What is claimed is:

1. A system for modeling of force vectors for a cast to correct orthopedic deformities, the system is programmed to execute machine readable instructions to:
   receive an image of the deformity;
   generate a three-dimensional model of the deformity based the image of the deformity;
   determine boundary conditions of the deformity using a machine learning model, wherein the machine learning model is trained on a plurality of prior patient data including an original image of the deformity of the patients, intermediate images of the deformity of the patients and an image of the final corrected deformity of the patient;
   determine a series of steps for correcting the deformity based on the machine learning model and the determined boundary conditions; and
   generate a force vector for a next series cast based on a series of automated finite-element-analysis simulations to minimize the deviation between the determined boundary condition and the predicted correction as determined using finite element analysis.

2. The system of claim 1, wherein the system includes a camera.

3. The system of claim 2, wherein the camera is at least one of an array of cameras, an ultrasound, a three-dimensional scanner, a magnetic resonance imaging device, or a CT scan.

4. The system of claim 1, wherein the prior patient data includes a plurality of scans of prior discarded casts of patients to determine the original deformity, stages of correction of the deformity and the final corrected deformity.

5. The system of claim 1, wherein to generate a force vector for a next series cast the system is programmed to:
determine a finite element analysis machine learning model based on a point cloud of force vectors determined from prior simulations for a plurality of patients; and
use the finite element analysis machine learning model for finite element analysis.

6. The system of claim 1, wherein to generate a force vector for a next series cast the system is programmed to:
correct the deformity in more than one direction in the next series cast simultaneously.

7. The system of claim 1, wherein to generate a force vector for a next series cast the system is programmed to:
correct the deformity in three dimensions in each direction in the next series cast simultaneously for each plane of corrections.

8. A method for modeling of force vectors for serial casts to correct orthopedic deformities, the method comprising:
receiving an image of the deformity;
generating a three-dimensional model of the deformity based the image of the deformity;
determining boundary conditions of the deformity using a machine learning model, wherein the machine learning model is trained on a plurality of prior patient data including an original image of the deformity of the patients, intermediate images of the deformity of the patients and an image of the final corrected deformity of the patient;
determining a series of steps for correcting the deformity based on the machine learning model and the determined boundary conditions; and
generating a force vector for a next series cast based on a series of automated finite-element-analysis simulations to minimize the deviation between the determined boundary condition and the predicted correction as determined using finite element analysis.

9. The method of claim 8, wherein the image of the deformity is acquired via a camera.

10. The method of claim 9, wherein the camera is at least one of an array of cameras, an ultrasound, a three-dimensional scanner, a magnetic resonance imaging device, or a CT scan.

11. The method of claim 8, wherein the prior patient data includes a plurality of scans of prior discarded casts of patients to determine the original deformity, stages of correction of the deformity and the final corrected deformity.

12. The method of claim 8, wherein the method further comprises:
determining a finite element analysis machine learning model based on a point cloud of force vectors determined from prior simulations for a plurality of patients; and
using the finite element analysis machine learning model for finite element analysis.

13. A non-transitory computer readable medium storing instructions executable by a processing device, wherein execution of the instructions causes the processing device to implement a method for modeling of force vectors for serial casts to correct orthopedic deformities, the method comprising:
receiving an image of the deformity;
generating a three-dimensional model of the deformity based the image of the deformity;
determining boundary conditions of the deformity using a machine learning model, wherein the machine learning model is trained on a plurality of prior patient data including an original image of the deformity of the patients, intermediate images of the deformity of the patients and an image of the final corrected deformity of the patient;
determining a series of steps for correcting the deformity based on the machine learning model and the determined boundary conditions; and
generating a force vector for a next series cast based on a series of automated finite-element-analysis simulations to minimize the deviation between the determined boundary condition and the predicted correction as determined using finite element analysis.

\* \* \* \* \*